(12) United States Patent
Forster

(10) Patent No.: US 11,805,985 B2
(45) Date of Patent: Nov. 7, 2023

(54) STEREO ENDOSCOPE

(71) Applicant: KARL STORZ SE & Co. KG, Tuttlingen (DE)

(72) Inventor: Jonas Forster, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 387 days.

(21) Appl. No.: 17/094,186

(22) Filed: Nov. 10, 2020

(65) Prior Publication Data

US 2021/0137365 A1    May 13, 2021

(30) Foreign Application Priority Data

Nov. 13, 2019   (DE) .................... 10 2019 130 593.4

(51) Int. Cl.
*A61B 1/00* (2006.01)
*A61B 1/05* (2006.01)

(52) U.S. Cl.
CPC ............ *A61B 1/00193* (2013.01); *A61B 1/05* (2013.01)

(58) Field of Classification Search
CPC ......... A61B 1/00193; A61B 1/05; A61B 1/04; A61B 1/0008; A61B 1/00163; A61B 1/00174; A61B 1/00183; A61B 1/00101
USPC ....................................................... 600/111
See application file for complete search history.

(56) References Cited

U.S. PATENT DOCUMENTS

| 4,873,572 | A | 10/1989 | Miyazaki et al. |
| 2002/0068853 | A1* | 6/2002 | Adler ................. A61B 1/00082 600/109 |
| 2013/0038689 | A1 | 2/2013 | McDowall |
| 2013/0041226 | A1 | 2/2013 | McDowall |
| 2017/0245744 | A1 | 8/2017 | McDowall |
| 2018/0196251 | A1 | 7/2018 | Duckett, III |
| 2018/0270453 | A1* | 9/2018 | Kupferschmid ... A61B 1/00188 |
| 2020/0228787 | A1* | 7/2020 | Heni .................. A61B 1/00183 |
| 2020/0229685 | A1* | 7/2020 | Wieters ............. A61B 1/00096 |

FOREIGN PATENT DOCUMENTS

| DE | 10 2017 123896 A1 | 10/2017 |
| WO | 2019/072685 A1 | 4/2019 |

OTHER PUBLICATIONS

Search Report, DE 10 2019 130 593.4, Apr. 3, 2020 (8 pp.).
Add 3D Capabilities to Your Image1 S™ Dynamic Camera Architecture, Karl Storz (2 pp.).
Search Report, EP 20206956.3, Jan. 13, 2021 (9 pp.).

* cited by examiner

*Primary Examiner* — Timothy J Neal
*Assistant Examiner* — James Edward Boice
(74) *Attorney, Agent, or Firm* — Eversheds Sutherland (US) LLP

(57) ABSTRACT

A stereo endoscope for capturing a first image which is provided to be observed by a first eye and a second image which is provided to be observed by a second eye, including a shaft with a distal end region, a first image sensor in the distal end region of the shaft, for capturing the first image, and a second image sensor in the distal end region of the shaft, for capturing the second image. The first image sensor and the second image sensor are arranged offset relative to one another in a direction which is parallel to at least either a light-sensitive layer of the first image sensor or a light-sensitive layer of the second image sensor and which is orthogonal to a longitudinal axis the distal end region of the shaft. The first image sensor and the second image sensor are oriented in opposite directions.

16 Claims, 4 Drawing Sheets

STEREO ENDOSCOPE

TECHNICAL FIELD

The present invention relates to a stereo endoscope for capturing an image which is provided to be observed by the left eye and an image which is provided to be observed by the right eye. The present invention relates, in particular, to a stereo endoscope in which the image sensors for capturing the two images are arranged in a distal end region of the stereo endoscope.

BACKGROUND OF THE INVENTION

In an endoscope, the image generated at the distal end by an objective can be transmitted by a relay lens system, a coherent bundle of optical fibers or in any other way to the proximal end and can be captured there by an integrated or mechanically and optically coupled camera, and a corresponding image signal can be produced. Alternatively, the image generated by the objective are captured by an image sensor arranged close to the distal end, and a corresponding image signal can be produced. This applies equally to monocular endoscopes and stereoscopic endoscopes.

The arrangement of two image sensors in a distal end region of an endoscope, in particular, represents a technical challenge. This challenge increases with increasing miniaturization. There are a number of approaches for arranging two image sensors that are as large as possible in an installation space that is as small as possible.

U.S. Pat. No. 4,873,572 describes a plurality of electronic endoscopes, each with two image sensors 214a, 214b; 264a, 264b; 293a, 293b or two imaging regions 21, 22 (abstract; column 4, lines 16 to 26; column 12, lines 12 to 16; column 15, lines 22 to 33; column 16, line 53 to column 17, line 3; FIGS. 1, 10, 12, 15 to 18, 20 to 22). The two image sensors 214a, 214b; 264a, 264b; 293a, 293b or two imaging regions 21, 22 are arranged next to one another or back-to-back.

U.S. Pat. No. 5,689,365 describes stereo endoscopes, each with two image sensors 18; 18L, 18R arranged next to one another (FIGS. 4, 5, 7, 8, 10, 13, 17 to 20, 23, 25, 27, 28, 32, 33).

DE102017123896A1 has disclosed a stereo endoscope, in which two image sensors are arranged parallel to and offset from one another in the shaft. The stereo base of the instrument is aligned parallel to the sensors.

SUMMARY OF THE INVENTION

An object of the present invention consists of developing an improved endoscope, in particular an improved stereo endoscope.

This object is achieved by the subject matter of the independent claims.

Developments are specified in the dependent claims.

A stereo endoscope for capturing a first image which is provided to be observed by a first eye and a second image which is provided to be observed by a second eye comprises a shaft with a distal end region, a first image sensor in the distal end region of the shaft, for capturing the first image, and a second image sensor in the distal end region of the shaft, for capturing the second image, wherein the distal end region of the shaft comprises two components that are the same or substantially the same, which are arranged next to one another and joined to one another and which form an outer surface region of the distal end region. Each of the two components comprises one of the two beam paths of the stereo endoscope, in particular.

In particular, the two components each have a cylindrical form and a semicircular or substantially semicircular cross section. The two components can form the entire distal end region or part of the distal end region. Below, a cylinder or the term "cylindrical" is understood to mean a general cylinder, as defined in mathematics. Mathematics defines a general cylinder as a geometric body which is delimited by a cylinder surface and two parallel planes. Here, a cylinder surface is understood to be a surface consisting of all straight lines g of the space which each have a common point with a specified curve k, the directrix of the cylinder surface, and which are parallel to a specified straight line g0, which likewise intersects k. These straight lines are referred to as the generatrices of the cylinder surface. A right circular cylinder is a special case of the general cylinder. However, the general definition of the cylinder is meant in the present case.

A stereo endoscope for capturing a first image which is provided to be observed by a first eye and a second image which is provided to be observed by a second eye comprises a shaft with a distal end region, a first image sensor in the distal end region of the shaft, for capturing the first image, and a second image sensor in the distal end region of the shaft, for capturing the second image, wherein both the light-sensitive layer of the first image sensor and the light-sensitive layer of the second image sensor are arranged parallel or substantially parallel to a longitudinal axis of the distal end region, wherein the first image sensor and the second image sensor are oriented in opposite directions, wherein the first image sensor and the second image sensor are arranged offset relative to one another in a direction which is orthogonal to a longitudinal axis of the distal end region of the shaft and parallel to at least either a light-sensitive layer of the first image sensor or a light-sensitive layer of the second image sensor.

The stereo endoscope is provided and embodied, in particular, for the use in microinvasive measures or for other medical purposes. Alternatively, the stereo endoscope can be provided and embodied for non-medical purposes. The stereo endoscope can comprise one or more work channels, through which the fluids can be conducted or medical instruments can be guided, or it can be embodied as a trocar sleeve.

The shaft of the stereo endoscope can have a straight or bent, rigid or flexible embodiment. In particular, the distal end region of the shaft has a rigid and straight embodiment such that the outer lateral surface of the distal end region is cylindrical. The cross section of the distal end region is circular, in particular. In particular, the longitudinal axis of the distal end region is the axis of symmetry, with respect to which the outer lateral surface of the distal end region is translationally symmetric and/or rotationally symmetric.

The first image sensor is provided, in particular, to capture an image provided to be observed by the left eye, with this image also being referred to as left image. The second image sensor is provided, in particular, to capture an image provided to be observed by the right eye, with this image also being referred to as right image.

Each of the two image sensors has a thin layer-shaped light-sensitive image capture region, which is also referred to as light-sensitive layer. The thin layer-shaped image capture region is plane and rectangular, in particular. The image capture region of each image sensor can have portions sensitive to different wavelength ranges within the same plane or within a plurality of different planes. The layer-shaped image capture regions or light-sensitive layers of each image sensor are arranged, in particular, parallel or substantially parallel to a longitudinal axis of the distal end region of the shaft of the stereo endoscope.

In particular, the layer-shaped image capture region of each image sensor is arranged tightly below (i.e., downstream in the direction of light propagation) a light entry surface of the image sensor. The opposite orientation of the image sensors means, in particular, an opposite orientation of the light entry surfaces of the image sensors. Two directions are opposite if they include an angle of at least 120 degrees, in particular if they include an angle of at least 150 degrees or at least 170 degrees, or of 180 degrees.

The arrangement of the image sensors offset in the direction described is an arrangement of the image sensors next to one another or substantially next to one another. The arrangement of the image sensors substantially next to one another but with an opposite or substantially opposite orientation can facilitate a particularly good use of available installation space and hence a particularly good ratio between the size of the sensors and the size of the required installation space.

In a stereo endoscope as described herein, a light-sensitive layer of the first image sensor and a light-sensitive layer of the second image sensor are arranged offset relative to one another, in particular in a direction which is orthogonal to the light-sensitive layers of both image sensors and orthogonal to a longitudinal axis of the distal end region of the shaft.

The arrangement of the image sensors with opposite or substantially opposite orientation offset not only in the direction parallel to at least one light-sensitive layer but also in the direction orthogonal to at least one light-sensitive layer can facilitate a particularly good use of available installation space and hence a particularly good ratio between the size of the sensors and the size of the required installation space. Using this, it is possible to realize a stereo endoscope with a particularly small diameter.

In a stereo endoscope as described herein, the light-sensitive layer of the first image sensor is arranged offset relative to the light-sensitive layer of the second image sensor, in particular immediately before the incidence on the first image sensor in the direction of light propagation of light.

Alternatively, the light-sensitive layer of the first image sensor is arranged offset relative to the light-sensitive layer of the second image sensor, immediately before the incidence on the first image sensor counter to the direction of light propagation of light.

The direction of light propagation means the direction of propagation of light, which emanates from an object to be observed and propagates along the optical axis of a beam path leading to the respective image sensor. In this case, the optical axis can change its direction, in particular at reflecting surfaces. Between reflecting surfaces, the optical axis is straight, in particular, and corresponds, for example, to the axis of symmetry of lenses in the case of a rotationally symmetric lenses. Particularly in the case of non-rotationally symmetric lenses, the mean propagation direction of light, which emanates from observed objects and which contributes to the generation of an image in the relevant image sensor, can be used alternatively as the direction of light propagation.

The direction of light propagation of light immediately before said light is incident on an image sensor is, in particular, the direction of light propagation of the light between a last reflecting surface and the light-sensitive layer of the image sensor. In particular, this direction of light propagation is orthogonal or substantially orthogonal to the longitudinal axis of the distal end region of the shaft.

A stereo endoscope as described herein comprises, in particular, a first reflecting surface for reflecting light, a second reflecting surface for reflecting light, a first beam path with a first straight section, which extends along the direction of light propagation to the first reflecting surface, and a second straight section, which extends from the first reflecting surface to the first image sensor, and a second beam path with a first straight section, which extends along the direction of light propagation to the second reflecting surface, and a second straight section, which extends from the second reflecting surface to the second image sensor, wherein the first straight section and the second straight section of the first beam path are arranged in a first beam path plane, wherein the first straight section and the second straight section of the second beam path are arranged in a second beam path plane, which differs from the first beam path plane, and wherein a direction of light propagation of light in the second straight section of the first beam path and a direction of light propagation of light in the second straight section of the second beam path are opposite or substantially opposite to one another.

A stereo endoscope for capturing a first image which is provided to be observed by a first eye and a second image which is provided to be observed by a second eye comprises a shaft with a distal end region, a first image sensor in the distal end region of the shaft, for capturing the first image, a second image sensor in the distal end region of the shaft, for capturing the second image, a first reflecting surface for reflecting light, a second reflecting surface for reflecting light, a first beam path with a first straight section, which extends along the direction of light propagation to the first reflecting surface, and a second straight section, which extends from the first reflecting surface to the first image sensor, and a second beam path with a first straight section, which extends along the direction of light propagation to the second reflecting surface, and a second straight section, which extends from the second reflecting surface to the second image sensor, wherein the first straight section and the second straight section of the first beam path are arranged in a first beam path plane, wherein the first straight section and the second straight section of the second beam path are arranged in a second beam path plane, which differs from the first beam path plane, and wherein a direction of light propagation of light in the second straight section of the first beam path and a direction of light propagation of light in the second straight section of the second beam path are opposite or substantially opposite to one another. Otherwise, the stereo endoscope can have the same or similar properties as the remaining stereo endoscopes described herein.

In relation to the direction of light propagation, the first reflecting surface is arranged immediately upstream of the first image sensor within the meaning of no further reflecting surface being arranged between the first reflecting surface and the first image sensor. Light propagates in a straight line or substantially in a straight line between the first reflecting surface and the first image sensor and, in particular, is at best refracted at the interfaces between different materials. In relation to the direction of light propagation, the second reflecting surface is arranged immediately upstream of the second image sensor within the meaning of no further reflecting surface being arranged between the second reflecting surface and the second image sensor. Light propagates in a straight line or substantially in a straight line between the second reflecting surface and the second image sensor and, in particular, is at best refracted at the interfaces between different materials.

In the direction of light propagation upstream of the first reflecting surface, light propagates along the optical axis of the first beam path, in particular. The optical axis of the first beam path is parallel or substantially parallel to a longitudinal axis of the distal end region of the shaft upstream of the first reflecting surface, in particular. In the direction of light propagation upstream of the second reflecting surface, light propagates along the optical axis of the second beam path, in particular. The optical axis of the second beam path is parallel or substantially parallel to a longitudinal axis of the distal end region of the shaft upstream of the second reflecting surface, in particular.

In a stereo endoscope as described herein, the first image sensor and the second image sensor are further arranged offset relative to one another, in particular, in a direction which is parallel to at least either a light-sensitive layer of the first image sensor or a light-sensitive layer of the second image sensor and orthogonal to a longitudinal axis of the distal end region of the shaft, with the first image sensor and the second image sensor being oriented in opposite directions.

In a stereo endoscope as described herein, the first beam path plane and the second beam path plane are parallel, in particular.

In a stereo endoscope as described herein, a distance between the first beam path plane and the second beam path plane is less than, in particular, the length of a stereo base of the stereo endoscope and not equal to zero.

In a stereo endoscope as described herein, in particular, the first image sensor and the second image sensor are arranged at opposite corners of a parallelogram and the first reflecting surface and the second reflecting surface are arranged at two further opposite corners of the parallelogram in a plane that is orthogonal to a longitudinal axis of the distal end region of the shaft. Corners opposite to one another are non-adjacent corners.

Arranging an image sensor at a corner of a parallelogram means the arrangement of the center of the image capture region of the image sensor at the corner of the parallelogram. Arranging a reflecting surface at a corner of a parallelogram means that the center of the reflecting surface or the center of the region of the reflecting surface filled by light steered onto the image capture region of the image sensor or the point of intersection of the optical axis of the beam path with the reflecting surface is arranged at the corner of the parallelogram. The area of the parallelogram is greater than zero. The parallelogram can be a rectangle and, in particular, a square. Typically, the stereo endoscope contains no structures which reproduce the sides of the parallelogram. Thus, the parallelogram represents an imagined form and is not physically present. At the corners of the parallelogram at which the two reflecting surfaces, in particular the centers of the reflecting surfaces, are arranged, the sides of the parallelogram respectively form an acute angle. At the corners at which the two image sensors, in particular the centers of the light-sensitive areas of the image sensors, are arranged, the sides of the parallelogram respectively form an obtuse angle.

In some conventional stereo endoscopes, either the image sensors are arranged at adjacent corners of a rectangle and the reflecting surfaces are at arranged adjacent corners of the rectangle or the image sensors and the reflecting surfaces are arranged along a single straight line. However, this arrangement is disadvantageous as it takes up very much space. By contrast, all specified features of the invention facilitate a space-saving arrangement of the image sensors and reflecting surfaces within the restricted diameter of the endoscope shaft. As a result, it is possible to create stereo instruments with a particularly small diameter.

In a stereo endoscope as described herein, the first reflecting surface and the second reflecting surface are arranged, in particular, in two intersecting planes.

The two planes, in which the first reflecting surface and the second reflecting surface are arranged, are arranged orthogonal or substantially orthogonal to one another, in particular. The line of intersection of the plane in which the first reflecting surface is arranged and the plane in which the second reflecting surface is arranged intersects, in particular, the longitudinal axis of the distal end region of the shaft.

In a stereo endoscope as described herein, the second straight section of the first beam path is arranged next to the second image sensor, in particular.

In a stereo endoscope as described herein, the second straight section of the second beam path is arranged next to the first image sensor, in particular.

An image sensor is arranged next to the second straight section of a beam path if a plane, in which the light-sensitive layer of the image sensor is located, intersects the second straight section of the beam path.

In a stereo endoscope as described herein, a light-sensitive layer of the first image sensor is, in particular, neither parallel nor orthogonal to a base plane, in which the first straight section of the first beam path and the second straight section of the second beam path are located.

In the case of a stereo endoscope as described herein, a light-sensitive layer of the first image sensor is, in particular, neither parallel nor orthogonal to a stereo base of the stereo endoscope.

Arranging the light-sensitive layers of the image sensors either parallel or orthogonal to a stereo base is something many conventional stereo endoscopes have in common. In the case of the conventional horizontal reproduction of the stereo base, which is at least advantageous for spatial perception, the arrangement of the light-sensitive layers of the image sensors in a manner either parallel or orthogonal to the stereo base simplifies the processing of the image data. In particular, there is no need to rotate the captured image through an angle that is not a multiple of 90 degrees.

Dispensing with this restriction, i.e., the arrangement of the light-sensitive layers of the image sensors neither parallel nor orthogonal to the stereo base, increases the outlay because either the image data must be rotated or the screen or the projector for observing the stereo image must be arranged at an angle. However, at the same time, this allows larger image sensors to be arranged in the distal end region of the shaft or available image sensors to be arranged in a smaller installation space. Hence, it is possible to improve the ratio between, firstly, the resolution, i.e., the number of pixels or picture elements, and, secondly, the shaft diameter.

In the case of a stereo endoscope as described herein, an angle between a light-sensitive layer of the first image sensor and a stereo base of the stereo endoscope is, in particular, in a range from 10 degrees to 80 degrees or in a range from 20 degrees to 70 degrees or in a range from 30 degrees to 60 degrees or in a range from 40 degrees to 50 degrees.

In the case of a stereo endoscope as described herein, the first image sensor comprises, in particular, a first rectangular image capture region, wherein an image of a straight line parallel to a stereo base of the stereo endoscope is inclined in the light-sensitive layer of the first image sensor in relation to straight edge sections of the rectangular image capture regions.

This inclination requires the aforementioned rotation.

In the case of a stereo endoscope as described herein, the distal end region of the shaft comprises, in particular, two components which are the same or substantially the same and which each have a cylindrical form and a substantially semicircular cross section.

Particularly in the case of a stereo endoscope that does not look straight ahead but whose viewing direction includes an angle greater than zero with the longitudinal axis of the distal end region of the shaft, these two components can have differently oriented light entry surfaces and different beam paths immediately downstream of the light entry surfaces. In particular, reflecting surfaces immediately downstream of the light entry surfaces in both components are respectively inclined in opposite direction with respect to the component itself.

In the case of a stereo endoscope as described herein, each of the two components respectively contains, in particular, either the first beam path or the second beam path in full or to a large extent.

Each of the two components can contain a beam path in completely encapsulated fashion. Alternatively, each component can have a lateral opening or cutout, which is sealed by the respective other component.

In the case of a stereo endoscope as described herein, an interface between the two components is, in particular, neither parallel nor orthogonal to a stereo base of the stereo endoscope.

The interface between the two components can be plane or curved. In the case of a curved interface, no portion or a portion of the curved interface forming less than half of the interface is parallel or orthogonal to the stereo base, in particular.

In this way, it is possible to develop two mutually complementary components, which contain all necessary component parts of the stereo endoscope and arrange these in particularly space-saving fashion. Together, the two components form part of the shaft of the stereo endoscope with a diameter that is as small as possible.

In the case of a stereo endoscope as described herein, one of the components, in particular, comprises a substantially closed lateral surface and a cutout, which is open toward the other component and in which at least either the first image sensor or the second image sensor is arranged. Additionally, the circuit board of the first or second image sensor can be arranged in full or in part in the cutout.

In particular, the closed lateral surface has the form of a section of a lateral face of a cylinder with a circular cross section or any other cross section. Further, the first reflecting surface and at least parts of the first beam path, in particular, are arranged in the cutout. In particular, the cutout has the form of a pocket or a recess, which is open toward the interface between the components. The cutouts are closed by joining the components and the distal end region with a completely closed lateral surface arises.

Further, the distal end region can comprise one or more further components, which form the distal end surface of the shaft, for example.

In the case of an stereo endoscope as described herein, the first image sensor, which is arranged in the first component, or the circuit board thereof protrudes into a cutout in the second component and the second image sensor, which is arranged in the second component, or the circuit board thereof protrudes into a cutout in the first component.

Thus, additionally present free space in the respective opposite component is used to arrange component parts of the one component. such as the image sensor and/or its circuit board, which take up very much space in the cross section of the endoscope. As a result, the required installation space and hence the diameter of the instrument can be reduced further.

A stereo endoscope as described herein comprises, in particular, a prism with the first reflecting surface, wherein an edge of the prism, which is arranged parallel to the longitudinal axis of the distal end region of the shaft, is chamfered or beveled or rounded off.

A chamfer or a bevel or a rounding of an edge—in particular outside of the region of space taken up by the light beam contributing to the image generation—can reduce the installation space taken up by the prism and can facilitate a more compact structure. The chamfered or beveled or rounded-off edge of the prism is arranged, in particular, near an outer surface of the distal end region of the shaft.

In the case of a method for capturing a stereo image generated by means of a stereo endoscope, said stereo image comprising a first image which is provided to be observed by a first eye and a second image which is provided to be observed by a second eye, a first light beam emanating from an object to be observed is deflected in the stereo endoscope into a first direction and impinges on a first image sensor and a second light beam emanating from the object to be observed is deflected in the stereo endoscope into a second direction and impinges on a second image sensor, wherein the first direction and the second direction are opposite or substantially opposite to one another.

In particular, the method is implementable using a stereo endoscope as described herein. The stereo endoscope as described herein is provided and embodied, in particular, to carry out a method as described herein.

In a method as described herein, both the first direction and the second direction, in particular, are orthogonal or substantially orthogonal to a longitudinal axis of a distal end region of the stereo endoscope.

A method as described herein further comprises, in particular, a step of processing image signals generated by the image sensors, wherein the images represented by the image signals are rotated through a predetermined angle during the processing.

The predetermined angle, in particular, lies in a range from 30 degrees to 60 degrees, for example in a range from 40 degrees to 50 degrees. The predetermined angle corresponds, in particular, to the angle between the planes in which light-sensitive regions of the image sensors are located and the stereo base of the stereo endoscope In this way, the images recorded in rotated fashion on the sensor are adapted back to the stereo base plane.

In a method for producing a stereo endoscope with a plurality of beam paths, a plurality of alike components, which each comprise one or more components in one of the plurality of beam paths, are manufactured and subsequently joined in opposite or different orientations in order to form at least a part of an outer surface of a distal end region of the stereo endoscope.

Each of the plurality of components comprises, in particular, all or nearly all components of one of the plurality of beam paths.

In the case of two components, these are joined, in particular, with an opposite orientation. In the case of three components, these are joined, in particular, in orientations which in pairwise fashion respectively differ by 120 degrees.

By way of example, the components can differ at their distal ends in order to facilitate different directions of view.

BRIEF DESCRIPTION OF THE FIGURES

Embodiments will be explained in more detail below with reference to the attached figures. In detail.

DETAILED DESCRIPTION OF THE EMBODIMENTS

Figure 1:
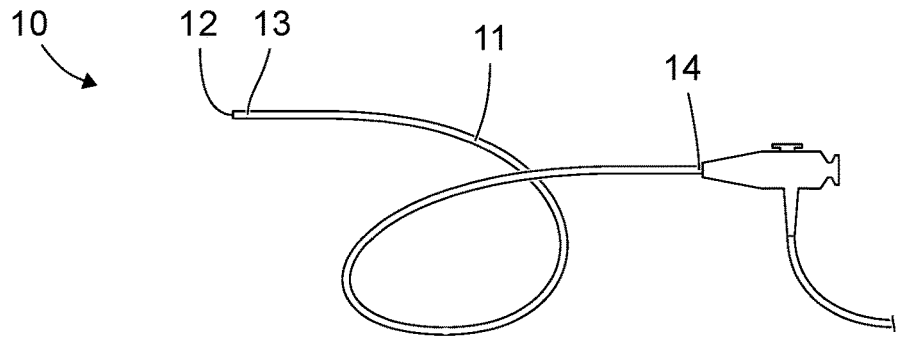
FIG. 1 shows a schematic illustration of a stereo endoscope.

FIG. 1 shows a schematic illustration of a stereo endoscope 10 comprising a shaft 11. The shaft 11 has a distal end 12, a distal end region 13 forming the distal end 12, and a proximal end 14. The shaft 11 is flexible between the proximal end 14 and the distal end region 13, i.e., it is non-destructively elastically or plastically deformable within structurally defined limits. The distal end region of 13 of the shaft 11 is rigid and straight. As an alternative and deviating from the illustration in FIG. 1, the shaft 11 can have a rigid and curved or rigid and straight embodiment.

Figure 2:
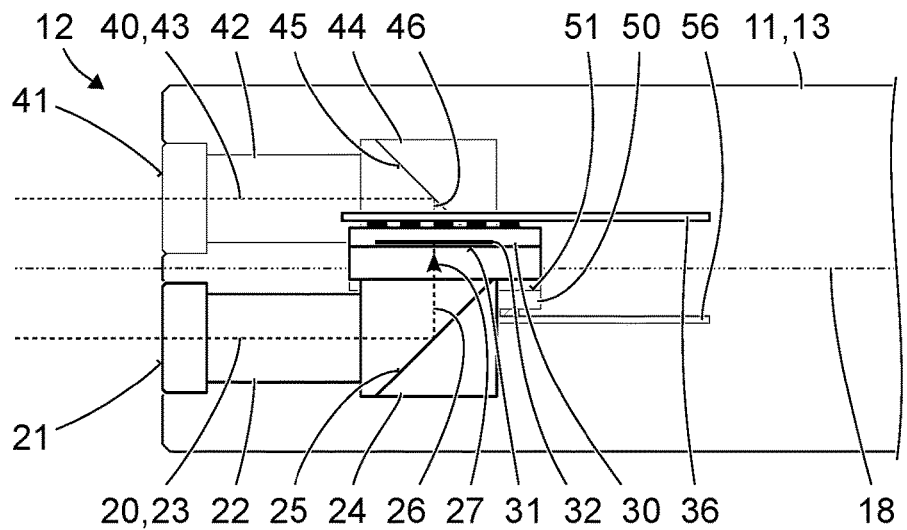
FIG. 2 shows a schematic illustration of a distal end region of the stereo endoscope of FIG. 1.

FIG. 2 shows an enlarged schematic illustration of the distal end region 13 of the shaft 11 of the stereo endoscope of FIG. 1. In FIG. 2, the distal end region 13 of the shaft 11 is represented in transparent fashion, i.e., only indicated by contours such that devices within the shaft 11 and the end region 13 are visible.

The illustrated example is a stereo endoscope which looks straight ahead, i.e., the viewing direction of which is parallel to the longitudinal axis 18 of the distal end region 13 of the shaft 11. The longitudinal axis 18 is the axis of symmetry, with respect to which the lateral surface of the distal end piece 13 is translationally symmetric and/or rotationally symmetric.

The distal end region 13 of the shaft 11 has a first beam path 20 to a first image sensor 30 for capturing a first image and a second beam path 40 to a second image sensor 50 for capturing a second image. For a simpler distinction, the optical and electronic components assigned to the first beam path are represented by relatively thick lines in FIG. 2 and the optical and electronic components assigned to the second beam path are illustrated in relatively thin lines.

The first image captured by means of the first image sensor 30 is provided, in particular, to be observed by the left eye and the second image captured by means of the second image sensor 50 is provided, in particular, to be observed by the right eye. In FIG. 2, the beam paths 20, 30 are indicated by the optical axes of optical components arranged in the beam paths 20, 30 or by the straight or reflected continuations of these optical axes.

The first beam path 20 comprises a first straight section 23 and a second straight section 26 within the distal end piece 13 of the shaft 11. The first straight section 23 of the first beam path 20 extends from a first light entry surface 21 up to a first reflecting surface 25 in a first prism 24. The first straight section 23 of the first beam path 20 extends predominantly within a first objective 22, which is indicated in a simplified fashion in FIG. 2 as a cylindrical element. The second straight section 26 of the first beam path 20 extends from the first reflecting surface 25 up to a thin layer-shaped light-sensitive region 32 below a light entry surface 31 of the first image sensor 30. The first straight section 23 of the first beam path 20 is parallel to the longitudinal axis 18 of the distal end region 13 of the shaft 11. Both straight sections 23, 26 of the first beam path 20 are parallel to the drawing plane of FIG. 2.

The first reflecting surface 25 is arranged at an angle of approximately 45 degrees with respect to the first section 23 of the first beam path 20. Therefore, the angle between the first section 23 and the second section 26 of the first beam path 20 is approximately 90 degrees. The thin layer-shaped light-sensitive region 32 of the first image sensor 30 is orthogonal to the second straight section 26 of the first beam path 20 and parallel to the longitudinal axis 18 of the distal end region 13 of the shaft 11.

The second beam path 40 comprises a first straight section 43 and a second straight section 46 within the distal end piece 13 of the shaft 11. The first straight section 43 of the second beam path 40 extends from a second light entry surface 41 up to a second reflecting surface 45 in a second prism 44. The first straight section 43 of the second beam path 40 extends predominantly within a second objective 42, which is indicated in a simplified fashion in FIG. 2 as a cylindrical element. The second straight section 46 of the second beam path 40 extends from the second reflecting surface 45 up to a thin layer-shaped light-sensitive region below a light entry surface 51 of the second image sensor 50. The first straight section 43 of the second beam path 40 is parallel to the longitudinal axis 18 of the distal end region 13 of the shaft 11. Both straight sections 43, 46 of the second beam path 40 are parallel to the drawing plane of FIG. 2.

The second reflecting surface 45 is arranged at an angle of approximately 45 degrees with respect to the first section 43 of the second beam path 40. Therefore, the angle between the first section 43 and the second section 46 of second first beam path 40 is approximately 90 degrees. The thin layer-shaped light-sensitive region 52 of the second image sensor 50 is orthogonal to the second straight section 46 of the second beam path 40 and parallel to the longitudinal axis 18 of the distal end region 13 of the shaft 11.

In a perspective illustrated in FIG. 2, the first beam path 20 is located above or in front of the longitudinal axis 18 of the distal end region 13 of the shaft 11 and the second beam path 40 is located therebelow or therebehind.

The first image sensor 30 is mechanically and electrically connected to a first circuit board 36 and the second image sensor 50 is mechanically and electrically connected to a second circuit board 56. The first circuit board 36 is arranged next to the second prism 44, i.e., it is located in a plane that intersects the second prism 44. In a perspective illustrated in FIG. 2, the first circuit board 36 therefore lies in front of or above the second prism 44, i.e., it partly conceals the second prism 44. The second circuit board 56 is arranged next to the second prism 24, i.e., it is located in a plane that intersects the first prism 24. In a perspective illustrated in FIG. 2, the second circuit board 56 therefore lies behind or below the second prism 24, i.e., it is partly concealed by the first prism 24.

The direction of propagation 27 of light, emanating from an observed object, in the second straight section 26 of the first beam path 20 is opposite to the direction of propagation of light, emanating from an observed object, in the second straight section 46 of the second beam path 40, which is largely concealed behind devices of the first beam path 20. Accordingly, the light entry surface is 31, 51 of the image sensors 30, 50 are oriented in opposite directions.

Figure 3:
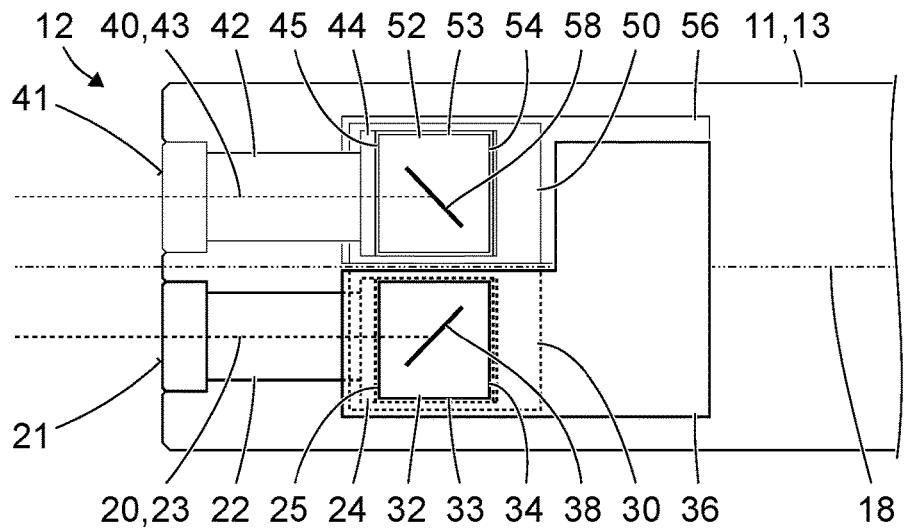
FIG. 3 shows a further schematic illustration of the distal end region of FIG. 2.

FIG. 3 shows a further schematic illustration of the distal end region 13 of FIG. 2. The type of illustration in FIG. 3 largely corresponds to that of FIG. 2; the drawing plane of FIG. 3 is likewise parallel to the longitudinal axis 18 of the distal end region 13 of the shaft 11 but orthogonal to the drawing plane of FIG. 2.

The circuit boards 36, 56 are arranged parallel to the drawing plane of FIG. 3. Each of the two circuit boards 36, 56 is L-shaped. In the perspective of FIG. 3, the first circuit board 36 is located in front of or above the second circuit board 56 and at least partly conceals the latter. In the perspective of FIG. 3, the first circuit board 36 is further located in front of or above the first image sensor 30 and the first prism 25 and completely conceals these. Therefore, the first image sensor 30 and the first prism 25 are not actually visible and only indicated by dashed lines in FIG. 3.

The thin layer-shaped light-sensitive regions 32, 52 of the image sensors 30, 50 are arranged within the image sensors and, moreover, concealed by the first circuit board 36 or the second prism 44 and are therefore not actually visible. Nevertheless, the contours of the thin layer-shaped light-sensitive regions 32, 52 of the image sensors 30, 50 are indicated by full lines in FIG. 3 in order to show their rectangular form with straight edge sections 33, 34, 53, 54. The thin layer-shaped light-sensitive regions 32, 52 of the image sensors 30, 50 are parallel to the drawing plane of FIG. 3.

The second straight section of the first beam path 20 and the second straight section of the second beam path 40 are orthogonal to the drawing plane of FIG. 3.

Further, the image 38 of the straight line parallel to the stereo base of the stereo endoscope is represented in the thin layer-shaped light-sensitive region 32 of the first image sensor 30 in FIG. 3 and the image 58 of the same straight line is represented in the thin layer-shaped light-sensitive region 52 of the second image sensor 50. Both the first reflecting layer 25 and the thin layer-shaped light-sensitive region 32 of the first image sensor 30 and also the second reflecting layer 45 and the thin layer-shaped light-sensitive region 52 of the second image sensor 50 are arranged at an angle to the stereo base of the stereo endoscope. Therefore, both the image 38 of the straight line in the thin layer-shaped light-sensitive layer 32 of the first image sensor 30 and the image 58 of the straight line in the thin layer-shaped light-sensitive layer 50 of the second image sensor 30 are arranged at an angle to the thin layer-shaped light-sensitive regions 32, 52 and are not parallel to any of the straight edge sections 33, 34, 53, 54 of the latter.

Figure 4:
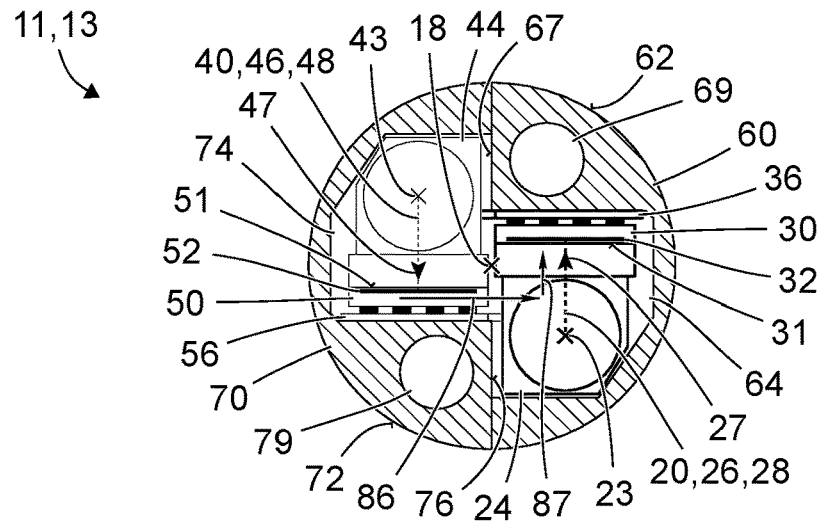
FIG. 4 shows a further schematic illustration of the distal end region of FIGS. 2 and 3.

FIG. 4 shows a schematic illustration of a section through the distal end region 13 of FIGS. 2 and 3. The sectional plane of FIG. 4 is orthogonal to the drawing planes of the FIGS. 2 and 3 and orthogonal to the longitudinal axis 18 of the distal end region 13 of the shaft 11. Hence, the sectional plane of FIG. 4 is further orthogonal to the first straight section 23 of the first beam path 20 and to the first straight section 43 of the second beam path 40.

The distal end region 13 of the shaft 11 comprises two components 60, 70, which form a mechanical structure and respectively one portion of the outer lateral surface of the distal end region 13. Surfaces of the components 60, 70 are illustrated in hatched fashion in FIG. 4.

The first component 60 has an outer lateral surface 62, which forms part of the outer lateral surface of the distal end region of 13 of the shaft 11. Further, the first component 60 has a cutout 64. The cutout 64 proceeds from a surface region 67 of the first component 60 facing the second component 70; i.e., it opens out toward the surface region 67 facing the second component 70. The first beam path 20, the first prism 24 with the first reflecting surface, and the first image sensor 30 are arranged in part or—like an example of FIG. 4—in full in the cutout 64 in the first component 60.

In the example illustrated in FIG. 4, a longitudinal edge (in the direction parallel to the longitudinal axis 18 of the distal end region 13 of the shaft 11 and consequently orthogonal to the drawing plane of FIG. 4) of the first prism 24 is chamfered or beveled outside of the space taken up by the beam. This reduces installation space taken up by the first prism 24 and facilitates a more compact structure.

The second component 70 has an outer lateral surface 72, which forms part of the outer lateral surface of the distal end region of 13 of the shaft 11. Further, the second component 70 has a cutout 74. The cutout 74 proceeds from a surface region 76 of the second component 70 facing the first component 60; i.e., it opens out toward the surface region 76 facing the first component 60. The second beam path 40, the second prism 44 with the first reflecting surface, and the second image sensor 50 are arranged in part or—like an example of FIG. 4—in full in the cutout 74 in the second component 70.

In the example illustrated in FIG. 4, a longitudinal edge (in the direction parallel to the longitudinal axis 18 of the distal end region 13 of the shaft 11 and consequently orthogonal to the drawing plane of FIG. 4) of the second prism 34 is chamfered or beveled outside of the space taken up by the beam. This reduces installation space taken up by the second prism 34 and facilitates a more compact structure.

In the case of the arrangement of the two components 60, 70 indicated in FIG. 4, these form a closed lateral surface of the distal end region 13 of the shaft. Joining the two components 60, 70—for example by laser welding—allows the two components 60, 70 to be connected to form a mechanical unit, which surrounds the beam paths 20, 40, the prisms 24, 44 with the reflecting surfaces 25, 45, and the image sensors of 30, 50—at least in the lateral direction—in a hermetically sealed fashion. At the distal end surface, the distal end region 13 in each component 60, 70 can comprise a window component, which has one of the two light entry faces 21, 41, inserted in hermetically sealed fashion and consequently can likewise be closed in hermetically sealed fashion.

In the example shown in FIG. 4, each of the two components 60, 70 further has a channel 69, 79 in the form of a bore parallel or substantially parallel to the longitudinal axis 18 of the distal end region 13 of the shaft 11. Optical fibers which transmit illumination light to the distal end of the shaft 11, said illumination light emerging there and illuminating an object to be observed, can be arranged in the channels 69, 79. As an alternative or in addition thereto, a fluid can flow and/or an instrument can be moved to the distal end of the stereo endoscope in the channels 69, 70 and/or in one or more further channels.

Figure 5:
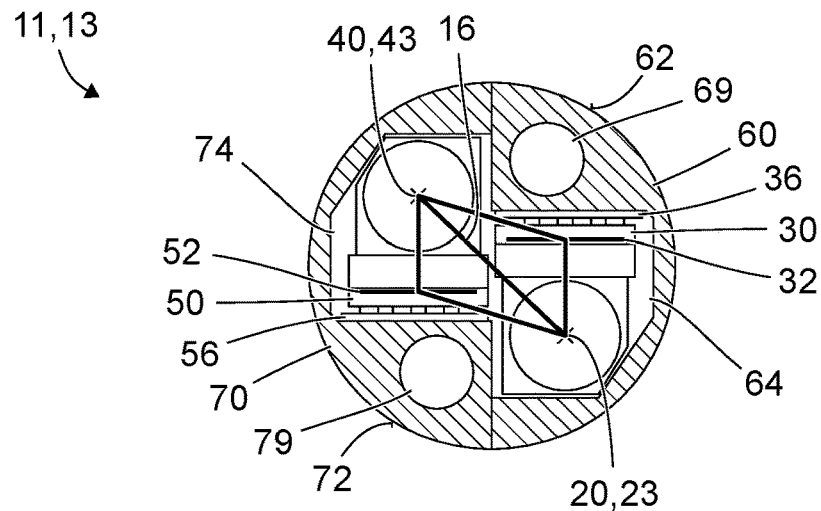
FIG. 5 shows a further schematic illustration of the distal end region of FIGS. 2 to 4.

FIG. 5 shows a further schematic illustration of the distal end region 13 of FIGS. 2 to 4. The illustration in FIG. 5 largely corresponds to the illustration in FIG. 4. Some reference signs have been omitted and the stereo base 16 of the stereo endoscope is indicated in FIG. 5. The stereo base is a straight connecting path of the points of intersection of the optical axes, which represent the beam paths 20, 40 here, with the light entry surfaces 21, 41.

Further, FIG. 5 illustrates a parallelogram, the corners of which are arranged by the centers of the reflecting surfaces (or of the components thereof involved in the transmission of light to the image sensors) and the centers of the thin layer-shaped light-sensitive regions 32, 52 of the image sensors 30, 50. The reflecting surfaces and the image sensors 30, 50 are arranged in alternating fashion at the corners of the parallelogram. The centers of the reflecting surfaces are arranged at two corners of the parallelogram that are opposite to one another. The centers of the light-sensitive regions 32, 52 of the image sensors 30, 50 are arranged at the other two corners of the parallelogram that are opposite to one another. At the corners at which the centers of the reflecting surfaces are arranged, the sides of the parallelogram respectively form an acute angle. At the corners at which the centers of the light-sensitive regions 32, 52 of the image sensors 30, 50 are arranged, the sides of the parallelogram respectively form an obtuse angle.

In particular, the parallelogram illustrated in FIG. 5 is not physically present in the distal end region 13. Thus, in particular, the distal end region has no structure which, for example, reproduces one of the sides of the parallelogram. Only the centers of the reflecting surfaces and of the image sensors 30, 50—which, as such, are not structurally distinguished either—form the corners of the imagined parallelogram.

Figure 6:
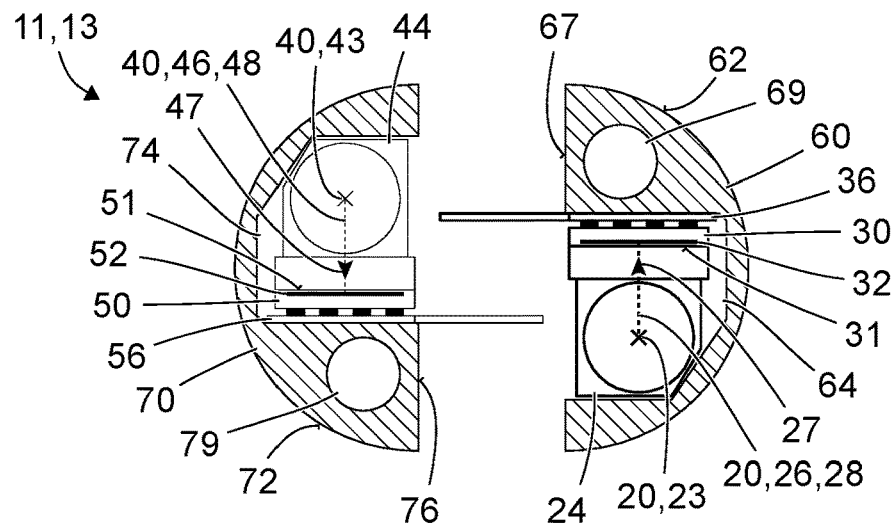
FIG. 6 shows a further schematic illustration of the distal end region of FIGS. 2 to 5.

FIG. 6 shows a further schematic illustration of the distal end region 13 of FIGS. 2 to 5. The type of illustration in FIG. 6 largely corresponds to that of FIGS. 4 and 5.

The illustration in FIG. 6 differs from the illustrations in FIGS. 4 and 5 in that, in particular, the components 60, 70 with the beam paths 20, 40, prisms 24, 44, reflecting surfaces, and image sensors 30, 50 arranged therein are arranged at a distance from one another. By way of example, the situation illustrated in FIG. 6 is present following insertion of the objectives, prisms 24, 44, and image sensors with the circuit boards 36, 56 into the cutouts 64, 74 of the components 60, 70 and directly before the two components 60, 70 are joined.

As already identifiable in FIGS. 3 to 5, it is also identifiable in FIG. 6 that the first prism 24 with the first reflecting surface 25, the first image sensor 30, and hence entire first beam path 20 is arranged in the cutout 64 in the first component 60. A large part of the first circuit board 36, to which the first image sensor 30 is mechanically and electrically connected, is also arranged in the cutout 64 in the first component 60. However, a part of the first circuit board 36 protrudes out of the cutout 64 in the first component 60. In the assembled configuration or situation shown in FIGS. 2 to 5, the part of the circuit board 36 protruding from the cutout 64 in the first component 60 is received in the cutout 74 in the second component 70.

The two components 60, 70, including the prisms 22, 44 and image sensors 30, 50 arranged therein, have, in particular, identical dimensions and mechanical, optical, and electrical properties and are merely arranged with an opposite orientation in space. Therefore, it applies accordingly to the second component 70 that the second prism 44 with the second reflecting surface 45, the second image sensor 50, and hence entire second beam path 40 is arranged in the cutout 74 in the second component 70. A large part of the second circuit board 56, to which the second image sensor 50 is mechanically and electrically connected, is also arranged in the cutout 74 in the second component 70. However, a part of the second circuit board 56 protrudes out of the cutout 74 in the second component 70. In the assembled configuration or situation shown in FIGS. 2 to 5, the part of the circuit board 56 protruding from the cutout 74 in the second component 70 is received in the cutout 64 in the first component 60.

In the example illustrated on the basis of FIGS. 1 to 6, the surface region 67 of the first component 60 facing the second component 70 and the surface region 76 of the second component 70 facing the first component 60 are plane in each case. In the assembled configuration or situation shown in FIGS. 2 to 5, the plane surface region 67 of the first component 60 and the plane surface region 76 of the second component 70 rest against one another—apart from the openings to the cutouts 64, 74—in planar fashion. At least the outer edges or edge regions of the surface regions 67, 76 facing one another and resting against one another are joined, for example by laser welding.

Figure 7:
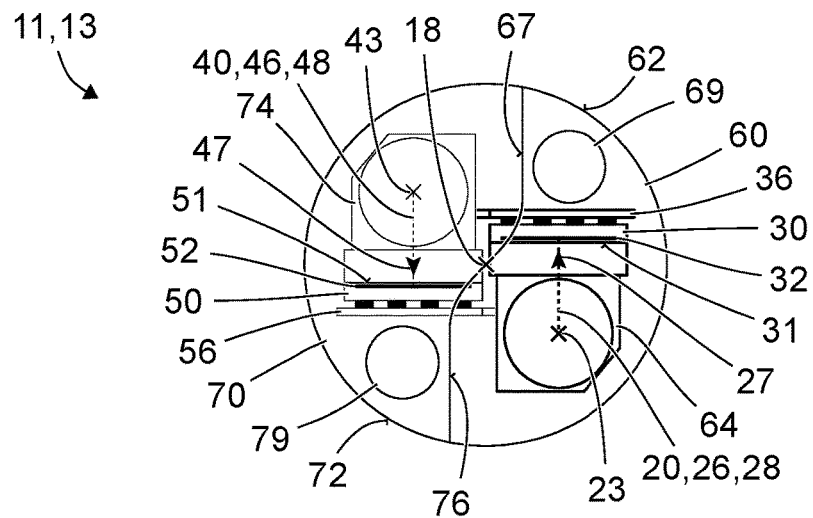
FIG. 7 shows a schematic illustration of a distal end region of a shaft of a further stereo endoscope.

FIG. 7 shows a schematic illustration of a distal end region 13 of a shaft 11 of a further stereo endoscope, which can be similar in terms of features, properties and functions to the stereo endoscope illustrated on the basis of FIGS. 1 to 6. The drawing plane of FIG. 7 is parallel to the sectional planes of the FIGS. 4, 5, and 6 and orthogonal to the longitudinal axis 18 of the distal end region 13 of the shaft 11. Unlike FIGS. 4, 5 and 6, FIG. 7 does not show a section but a frontal plan view.

In particular, features, properties, and functions in terms of which the distal end region 13 of the shaft 11 shown in FIG. 7 differs from the distal end region of the shaft of the stereo endoscope illustrated on the basis of FIGS. 1 to 6 are described below.

The distal end region 13 of the shaft 11 of the stereo endoscope 10 shown in FIG. 7 differs from the distal end region of the shaft of the stereo endoscope illustrated on the basis of FIGS. 1 to 6 in that, in particular, the interface between the components 60, 70 is not plane but curved. The surface region 67 of the first component 60 facing the second component 70 and the surface region 76 of the second component 70 facing the first component 60 are curved—apart from the openings to the cutouts 64, 74—in a manner corresponding to one another. Therefore, in the example shown in FIG. 7, too, the surface region 67 of the first component 60 and the surface region 76 of the second component 70 rest against one another—apart from the openings to the cutouts 64, 74—in planar fashion. At least the outer edges or edge regions of the surface regions 67, 76 facing one another are joined, for example by laser welding.

In the example shown in FIG. 7, the curved surface regions 67, 76 of the components respectively are cylindrically symmetric, i.e., translationally invariant in relation to translation parallel to the longitudinal axis 18 of the distal end region 13 of the shaft 11.

The curvature of the surface regions 67, 76 that face one another and—apart from the openings to the cutouts 64, 74—rest against one another can simplify the manufacture, in particular the generation of the cutouts 64, 74, and, for example, can make it easier to increase the size of the cutouts 64, 74 in comparison with the case of plane surface regions.

Figure 8:
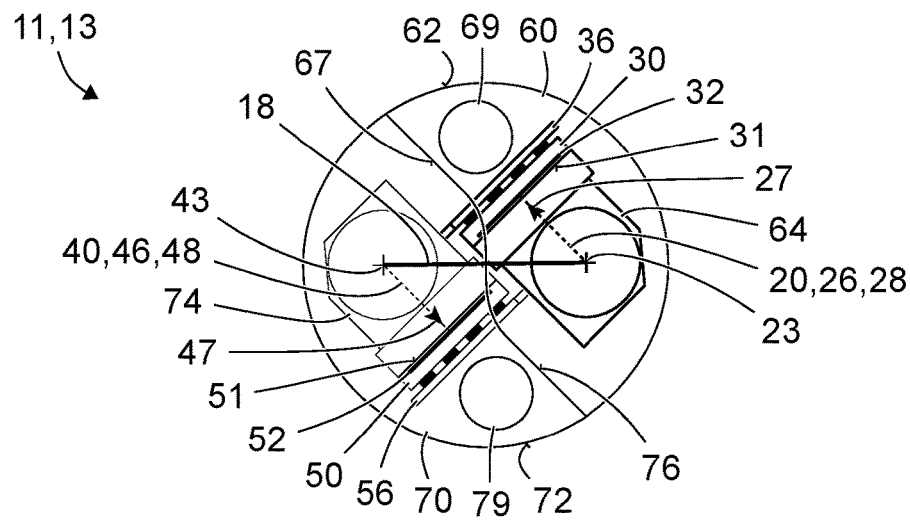
FIG. 8 shows a further schematic illustration of the distal end region of FIG. 7.

FIG. 8 shows a further schematic illustration of the distal end region 13 of the shaft 11 of FIG. 7. The type of illustration in FIG. 8 largely corresponds to that of FIG. 7. In particular, the drawing plane of FIG. 8 corresponds to the drawing plane of FIG. 7.

The illustration in FIG. 8 differs from the illustration in FIG. 7 in that the distal end region 13 of the shaft 11 is rotated about its longitudinal axis 18 such that the stereo base 16 of the stereo endoscope is arranged horizontally in FIG. 8. Further, a few reference signs have been omitted in FIG. 8.

Figure 9:
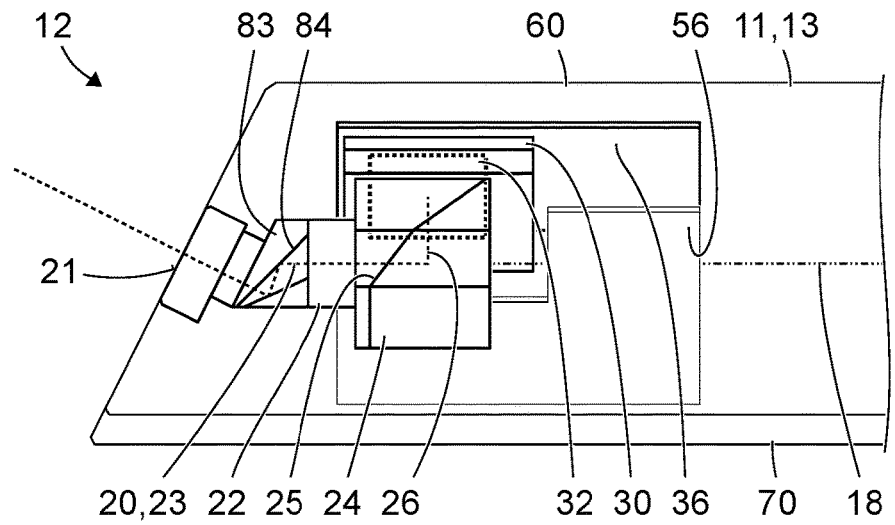
FIG. 9 shows a further schematic illustration of the distal end region of FIGS. 7 and 8.

FIG. 9 shows a further schematic illustration of the distal end region 13 of the shaft 11 of FIGS. 7 and 8. The type of illustration in FIG. 9 is similar to that of FIGS. 2 and 3. In particular, in FIG. 9, the distal end region 13 of the shaft 11 is represented in transparent fashion, i.e., only indicated by contours and the edge of the interface between the components 60, 70 such that the devices within the end region 13 of the shaft 11 are visible. The drawing plane of FIG. 9 is parallel to the longitudinal axis 18 of the distal end region 13 of the shaft 11, orthogonal to the drawing plane of FIG. 8 and—unlike the drawing planes of FIGS. 2 and 3—orthogonal to the stereo base of the stereo endoscope. In this illustration in FIG. 9, the two beam paths 20, 40 with the prisms 24, 44, the reflecting surfaces 25, 45, and the image sensors 30, 50 (cf. FIGS. 7 and 8) are exactly behind one another. Thus, the first beam path 30 conceals the second beam path. The edge of the first reflecting surface 25 at the outer surface of the prism 24 is visible in FIG. 9.

Further, FIG. 9 merely illustrates the second circuit board 56 and not the second image sensor, which is only largely, but not in fact completely concealed by the first prism 24 and the second circuit board 56.

The first prism 24, the first image sensor 30 and the circuit boards 36, 56 are visible in the perspective of FIG. 9 from the direction that is neither parallel nor orthogonal to the plane outer surface regions of these components (cf. FIG. 8).

It is clear from FIG. 9 that the viewing direction of the distal end region 13 of the shaft 11 shown in FIGS. 7 to 9 is not parallel to the longitudinal axis 18 of the distal end region 13 of the shaft 11, unlike in the case of the distal end region 13 illustrated on the basis of FIGS. 2 to 6. To this end, a viewing direction prism 83 with a plurality of reflecting surfaces 84 is provided in the first beam path 20. The viewing direction prism 83 is arranged distally from the first prism 24 such that all reflecting surfaces 84 of the viewing direction prism 83 are orthogonal to the drawing plane of FIG. 9. Therefore, the entire first beam path is distal—i.e., upstream in the direction of light propagation—of the first reflecting surface 25 of the first prism 24, in a plane parallel to the drawing plane of FIG. 9. The second straight section 26 of the first beam path 20, which is located downstream of the first reflecting surface 25 of the first prism 24 in the direction of light propagation, is not parallel to the drawing plane of FIG. 9.

A corresponding statement applies to the identical second beam path, which is, however, completely concealed by the first beam path 20 in FIG. 9.

In the example shown in FIGS. 7 to 9, the components 60, 70 together form the entire outer surface of the distal end region 13 of the shaft 11, i.e., also the distal end surface thereof.

Figure 10:
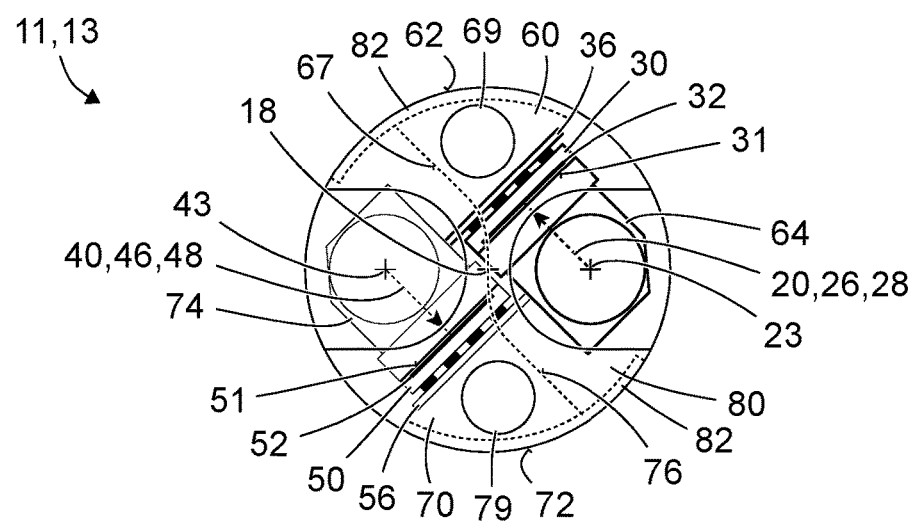
FIG. 10 shows a schematic illustration of a distal end region of a shaft of a further stereo endoscope.

FIG. 10 shows a schematic illustration of a distal end region 13 of a shaft 11 of a further stereo endoscope, which can be similar in terms of features, properties and functions to the stereo endoscope illustrated on the basis of FIGS. 1 to 6 and, in particular, to the stereo endoscope illustrated on the basis of FIGS. 7 to 9. The type of illustration in FIG. 10 corresponds to that of FIG. 7 and, in particular, FIG. 8. In particular, the drawing plane of FIG. 10 is orthogonal to the longitudinal axis 18 of the distal end region 13 of the shaft 11.

In particular, features, properties, and functions in terms of which the distal end region 13 of the shaft 11 shown in FIG. 10 differs from the distal end region of the shaft of the stereo endoscope illustrated on the basis of FIGS. 7 to 9 are described below.

The distal end region 13 of the shaft 11 of a stereo endoscope 10 shown in FIG. 10 differs from the distal end region of the shaft of the stereo endoscope illustrated on the basis of FIGS. 7 to 9 in that, in particular, the components 60, 70 do not form the entire outer surface of the distal end region 13 of the shaft 11. Instead, the components 60, 70 only form part of the lateral surface of the distal end region 13 of the shaft 11 and only parts of the distal end surface thereof, which faces the observer in the illustration of FIG. 10. Further parts of the outer surface of the distal end region 13 of the shaft 11 are formed by a third component 80 and by a fourth component 82. In the observation direction of FIG. 10, the third component 80 approximately has the form of a lying and many times substantially rounded-off capital letter "H" and forms a corresponding part of the front surface of the distal end region 13 of the shaft 11 of the stereo endoscope facing the observer in FIG. 10. The fourth component 82 forms part of the lateral surface of the stereo endoscope 10. The contours of thin-walled and tongue-shaped regions of the fourth component 82, which reach in the distal direction, are indicated in FIG. 10 by dashed lines.

Figure 11:
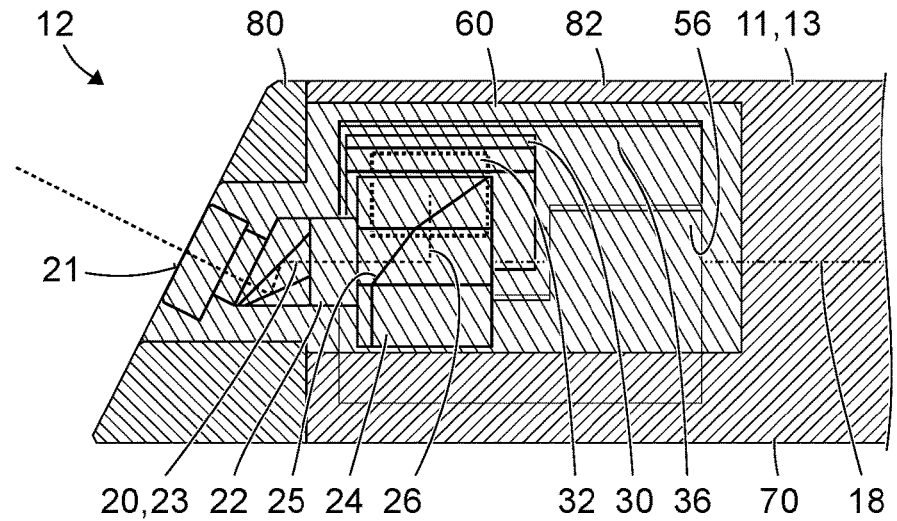
FIG. 11 shows a further schematic illustration of the distal end region of FIG. 10.

FIG. 11 shows a further schematic illustration of the distal end region 13 of the shaft 11 of FIG. 10. The type of illustration in FIG. 11 is similar to that of FIGS. 2 and 3 and, in particular, FIG. 9. In particular, in FIG. 11, the distal end region 13 of the shaft 11 is represented in transparent fashion, i.e., only indicated by contours such that devices within the end region 13 of the shaft 11 are visible. The drawing plane of FIG. 11 is parallel to the longitudinal axis 18 of the distal end region 13 of the shaft 11, orthogonal to the drawing plane of FIG. 10 and—like the drawing plane of FIG. 9—orthogonal to the stereo base of the stereo endoscope. In this illustration in FIG. 11, the two beam paths 20, 40 with the prisms 24, 44, the reflecting surfaces 25, 45, and the image sensors 30, 50 visible in FIG. 10 are exactly behind one another. Thus, the first beam path 20 conceals the second beam path.

Further, for reasons of clarity, FIG. 11 merely illustrates the second circuit board 56 and not the second image sensor, which is only largely, but not in fact completely concealed by the first prism 24 and the second circuit board 56.

The first component 60 and the second component, not visible in FIG. 11, only form part of the outer surface of the distal end region 13 of the shaft 11. To distinguish it from other components forming parts of the outer surface of the distal end region 13, the parts of the outer surface formed by the first component 60 is hatched steeply and wide, from top left to bottom right.

The third component 80 forms a large part of the distal end face and two portions (top and bottom in FIG. 11) of an adjoining ring-shaped region of the lateral surface. To distinguish it from the part of the outer surface formed by the first component 60, the part of the outer surface formed by the third component 80 is hatched tighter and flatter (from top left to bottom right). In the overview of FIGS. 10 and 11, it is possible to identify that the form of the third component 80 is an approximately circular section of a wedge. Two wide and deep grooves parallel to the longitudinal axis 18 of the distal end region 13, which emanate from opposite end regions, each have a horseshoe-shaped cross section in the example illustrated in FIGS. 10 and 11. These grooves are completely filled corresponding regions of the first component 60 and of the second component 70 with a corresponding form, which components surround the beam paths 20, 30.

At least the edges or edge regions of the interfaces between the third component 80 and the first component 60 and the second component 70 are joined, for example by laser welding.

A tubular fourth component 82 adjoins the first component 60 and the second component 70 in the proximal direction. To distinguish it from parts of the outer surface of the distal end region 13 of the shaft 11 formed by the first component 60 or the third component 80, the tubular fourth component 82 in FIG. 11 is hatched more tightly and from bottom left to top right. The distal end of the fourth component 82 has two tongues, which form the outer surface of the distal end region 13 between the parts of the outer surface formed by the first component 60 and the second component which is not visible in FIG. 11 and which adjoin the third component 80.

Deviating from the example illustrated on the basis of FIGS. 1 to 6, the surface regions 67, 76 of the components 60, 70 which rest again one another and are joined to one another can be curved, even in the case of a stereo endoscope 10 with a straight viewing direction, i.e., with a viewing direction parallel to the longitudinal axis of the distal end region 13 of the shaft 11. Deviating from the examples illustrated on the basis of FIGS. 7 to 11, the surface regions 67, 76 of the components 60, 70 which rest again one another and are joined to one another can be plane, even in the case of a stereo endoscope 10 with a straight viewing direction, i.e., with a viewing direction parallel to the longitudinal axis of the distal end region 13 of the shaft 11.

Deviating from the example illustrated on the basis of FIGS. 1 to 6, the outer surface of the distal end region 13 can be partly formed by a third component 80 or by a third component 80 and a fourth component 82 or by a plurality of further components, even in the case of the stereo endoscope 10 with a viewing direction parallel to the longitudinal axis 18 of the distal end region 13 of the shaft 11.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

REFERENCE SIGNS

10 Stereo endoscope
11 Shaft of the stereo endoscope 10
12 Distal end of the shaft 11
13 Distal end region of the shaft 11
14 Proximal end of the shaft 11
16 Stereo base of the stereo endoscope 10
18 Longitudinal axis of the distal end region 13 of the shaft
20 First beam path of the stereo endoscope 10
21 Light entry surface of the first beam path 20
22 Objective in the first beam path 20
23 First straight section of the first beam path 20
24 First prism in the first beam path 20
25 First reflecting surface in the first prism 24
26 Second straight section of the first beam path 20
27 Direction of light propagation in the first beam path 20
28 First beam path plane, in which the first beam path 20 is located
30 First image sensor of the stereo endoscope 10
31 Light entry surface of the first image sensor 30
32 Light-sensitive layer, light-sensitive region of the first image sensor 30
33 Straight edge section of the rectangular light-sensitive region 32
34 Straight edge section of the rectangular light-sensitive region 32
36 First circuit board, on which the first image sensor 30 is arranged
38 Image of a straight line parallel to the stereo base 16 of the stereo endoscope 10 in the light-sensitive layer 32 of the first image sensor 30
40 Second beam path of the stereo endoscope 10
41 Light entry surface of the second beam path 40
42 Objective in the second beam path 40
43 First straight section of the second beam path 40
44 Second prism in the second beam path 40
45 Second reflecting surface in the second prism 44
46 Second straight section of the second beam path 40
47 Direction of light propagation in the second beam path 40
48 Second beam path plane, in which the second beam path 40 is located
50 Second image sensor of the stereo endoscope 10
51 Light entry surface of the second image sensor 50
52 Light-sensitive layer, light-sensitive region of the first image sensor 50
53 Straight edge section of the rectangular light-sensitive region 52
54 Straight edge section of the rectangular light-sensitive region 52
56 Second circuit board, on which the second image sensor 50 is arranged
58 First image of a straight line parallel to the stereo base 16 of the stereo endoscope 10 in the light-sensitive layer 52 of the second image sensor 50
60 First component of the distal end region 13 of the shaft 11
62 Lateral surface of the first component 60
64 Cutout in the first component 60, in which the first reflecting surface 24 and the first image sensor 30 are arranged
67 Surface region of the first component 60 facing the second component 70
69 Channel for optical fibers for illumination light in the first component 60
70 Second component of the distal end region 13 of the shaft 11
72 Lateral surface of the second component 70
74 Cutout in the second component 70, in which the second reflecting surface 44 and the second image sensor 50 are arranged
76 Surface region of the second component 70 facing the first component 60
79 Channel for optical fibers for illumination light in the second component 70
80 Third component of the distal end region 13 of the shaft 11
82 Tubular fourth component of the distal end region 13 of the shaft 11

83 Viewing direction prism in the first beam path
84 Reflecting surface of the viewing direction prism in the first beam path
86 First direction, in which the image sensors are arranged offset relative to one another
87 Second direction, in which the image sensors are arranged offset relative to one another

I claim:

1. A stereo endoscope for capturing a first image which is provided to be observed by a first eye and a second image which is provided to be observed by a second eye, comprising:
   a shaft with a distal end region;
   a first image sensor in the distal end region of the shaft, for capturing the first image;
   a second image sensor in the distal end region of the shaft, for capturing the second image,
   wherein both the first image sensor and the second image sensor are arranged parallel or substantially parallel to a longitudinal axis of the distal end region,
   wherein the first image sensor and the second image sensor are oriented in opposite or substantially opposite directions,
   wherein the first image sensor and the second image sensor are arranged offset relative to one another in a first offset direction which is orthogonal to a longitudinal axis of the distal end region of the shaft, and
   wherein the first image sensor and the second image sensor are arranged further offset relative to one another in a second offset direction which is orthogonal to both image sensors and shaft to the first offset direction.

2. The stereo endoscope as claimed in claim 1, wherein the first image sensor has a first rectangular image capture region,
   an image of a straight line which is parallel to a stereo base of the stereo endoscope in the light-sensitive layer of the first image sensor is inclined in relation to straight edge sections of the rectangular image capture regions.

3. The stereo endoscope as claimed in claim 1, wherein the distal end region of the shaft comprises two components which are the same or substantially the same and which each have a cylindrical form and a substantially semicircular cross section.

4. The stereo endoscope as claimed in claim 3, wherein an interface between the two components is neither parallel nor orthogonal to a stereo base of the stereo endoscope.

5. The stereo endoscope as claimed in claim 3, wherein one of the components comprises:
   a substantially closed lateral surface,
   a cutout, which is open toward the other component and in which at least either the first image sensor or the second image sensor is arranged.

6. The stereo endoscope as claimed in claim 3, wherein the first image sensor, which is arranged in the first component, or the circuit board thereof protrudes into a cutout in the second component and the second image sensor, which is arranged in the second component, or the circuit board thereof protrudes into a cutout in the first component.

7. The stereo endoscope of claim 1, wherein the first image sensor and the second image sensor are equidistant from a distal end of the shaft in a direction parallel or substantially parallel to the longitudinal axis of the distal end region.

8. A stereo endoscope for capturing a first image which is provided to be observed by a first eye and a second image which is provided to be observed by a second eye, comprising:
   a shaft with a distal end region;
   a first image sensor in the distal end region of the shaft, for capturing the first image;
   a second image sensor in the distal end region of the shaft, for capturing the second image;
   a first reflecting surface for reflecting light;
   a second reflecting surface for reflecting light;
   a first beam path with a first straight section, which extends along the direction of light propagation to the first reflecting surface, and a second straight section, which extends from the first reflecting surface to the first image sensor;
   a second beam path with a first straight section, which extends along the direction of light propagation to the second reflecting surface, and a second straight section, which extends from the second reflecting surface to the second image sensor;
   wherein the first straight section and the second straight section of the first beam path are arranged in a first beam path plane,
   wherein the first straight section and the second straight section of the second beam path are arranged in a second beam path plane, which differs from the first beam path plane,
   wherein a direction of light propagation of light in the second straight section of the first beam path and a direction of light propagation of light in the second straight section of the second beam path are opposite or substantially opposite to one another;
   wherein a light-sensitive layer of the first image sensor and a light sensitive layer of the second image sensor are neither parallel nor orthogonal to a base plane, in which the first straight section of the first beam path and the first straight section of the second beam path are located.

9. The stereo endoscope as claimed in claim 8, wherein the first image sensor and the second image sensor are arranged at opposite corners of a parallelogram and the first reflecting surface and the second reflecting surface are arranged at two further opposite corners of the parallelogram in a plane that is orthogonal to a longitudinal axis of the distal end region of the shaft, wherein the sides of the parallelogram form an acute angle at the first opposite corners and form an obtuse angle at the two further opposite corners.

10. The stereo endo scope as claimed in claim 8, wherein the second straight section of the first beam path is arranged next to the second image sensor.

11. The stereo endoscope as claimed in claim 8, wherein the first image sensor has a first rectangular image capture region,
    an image of a straight line which is parallel to a stereo base of the stereo endoscope is inclined in the light-sensitive layer of the first image sensor in relation to straight edge sections of the rectangular image capture regions.

12. The stereo endoscope as claimed in claim 8, wherein the distal end region of the shaft comprises two components which are the same or substantially the same and which each have a cylindrical form and a substantially semicircular cross section.

13. The stereo endoscope as claimed in claim 12, wherein each of the two components respectively contains either the first beam path or the second beam path in full or to a large extent.

14. The stereo endoscope as claimed in claim 12, wherein an interface between the two components is neither parallel nor orthogonal to a stereo base of the stereo endo scope.

15. The stereo endoscope as claimed in claim 12, wherein one of the components comprises:
   a substantially closed lateral surface,
   a cutout, which is open toward the other component and in which at least either the first image sensor or the second image sensor is arranged.

16. The stereo endoscope as claimed in claim 12, wherein the first image sensor, which is arranged in the first component, or the circuit board thereof protrudes into a cutout in the second component and the second image sensor, which is arranged in the second component, or the circuit board thereof protrudes into a cutout in the first component.

* * * * *